United States Patent [19]

Sarian et al.

[11] 4,204,159

[45] May 20, 1980

[54] EDDY-CURRENT TEST PROBE WITH SEGMENTED CIRCUMFERENTIAL TEST GAP AND METHOD FOR INSPECTION OF MATERIALS

[76] Inventors: Suren Sarian, 145 N. El Camino Real #211, San Mateo, Calif. 94401; Duane P. Johnson, 702 El Granada Blvd., El Granada, Calif. 94018

[21] Appl. No.: 897,344

[22] Filed: Apr. 18, 1978

[51] Int. Cl.$^2$ ............................................. G01R 33/12
[52] U.S. Cl. ...................................... 324/232; 324/236
[58] Field of Search ............... 324/219, 220, 228, 232, 324/234, 236, 237–243, 262

[56] References Cited

U.S. PATENT DOCUMENTS

| | | | |
|---|---|---|---|
| 3,840,802 | 10/1974 | Anthony | 324/219 |
| 4,088,953 | 5/1978 | Sarian | 324/238 |
| 4,101,832 | 7/1978 | Baker et al. | 324/238 |

OTHER PUBLICATIONS

J. C. Spanner, "An Eddy Current Technique for Measuring the Tube to Tube Annulus in a Nuclear Test Reactor," *Non Distructive Testing,* Nov.–Dec. 1962, pp. 394–400.

*Primary Examiner*—Rudolph V. Rolinec
*Assistant Examiner*—Walter E. Snow
*Attorney, Agent, or Firm*—Delbert J. Barnard

[57] ABSTRACT

A plurality of eddy-current generators are angularly grouped about an axis within an inspection tool or probe. Each eddy-current generator presents a circumferentially extending test segment. Collectively, the test segments form a discontinuous test gap which extends circumferentially about the probe. In some embodiments, adapted for inspecting from the inside of tubing or fastener holes, the test gap is at the outer periphery of a probe. In other embodiments, adapted for inspecting from the outer surface portions of tubing, rods, etc., the test gap region extends around the inside of a central passageway formed through a support body. The eddy-current generators are supported for limited radial movement, enabling the tool or probe to adapt to differences in shape and dimension of the material being inspected. Each eddy-current generator combines low and high reluctance materials to (a) greatly reduce the mutual coupling of the several generators, (b) concentrate the reluctance of the eddy-current generators in the material to be tested, and (c) control the spatial extent and shape of generated eddy-currents.

26 Claims, 15 Drawing Figures

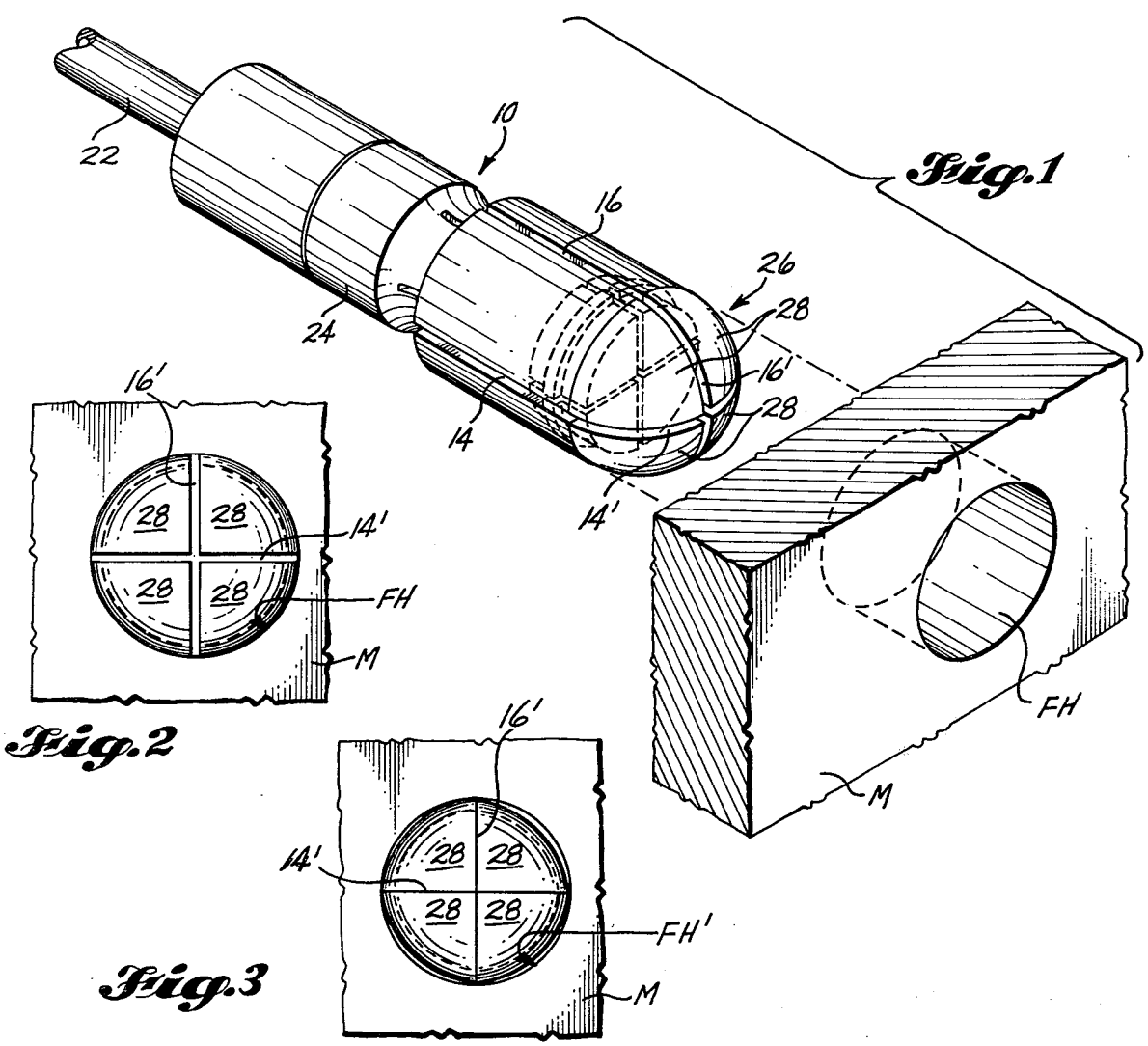
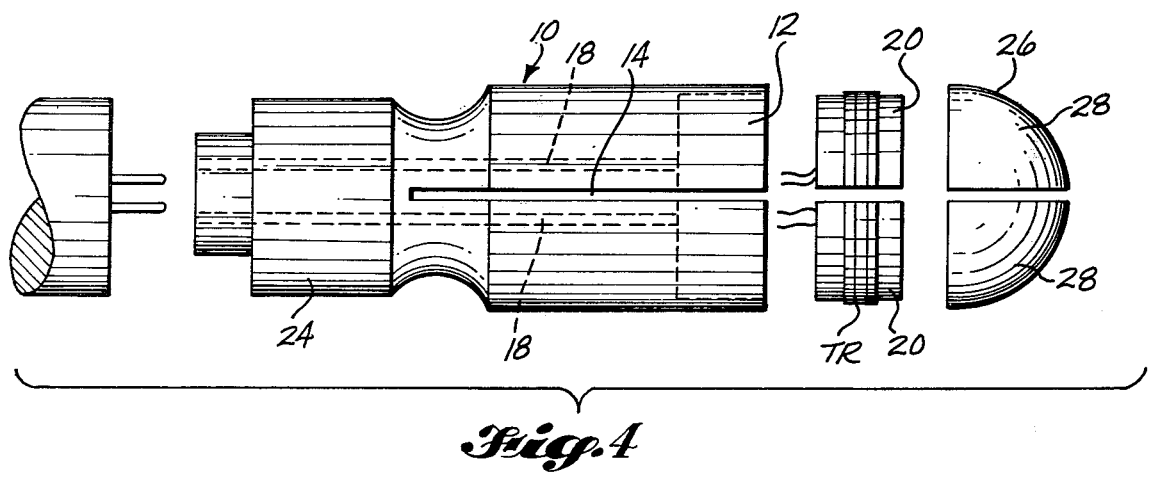

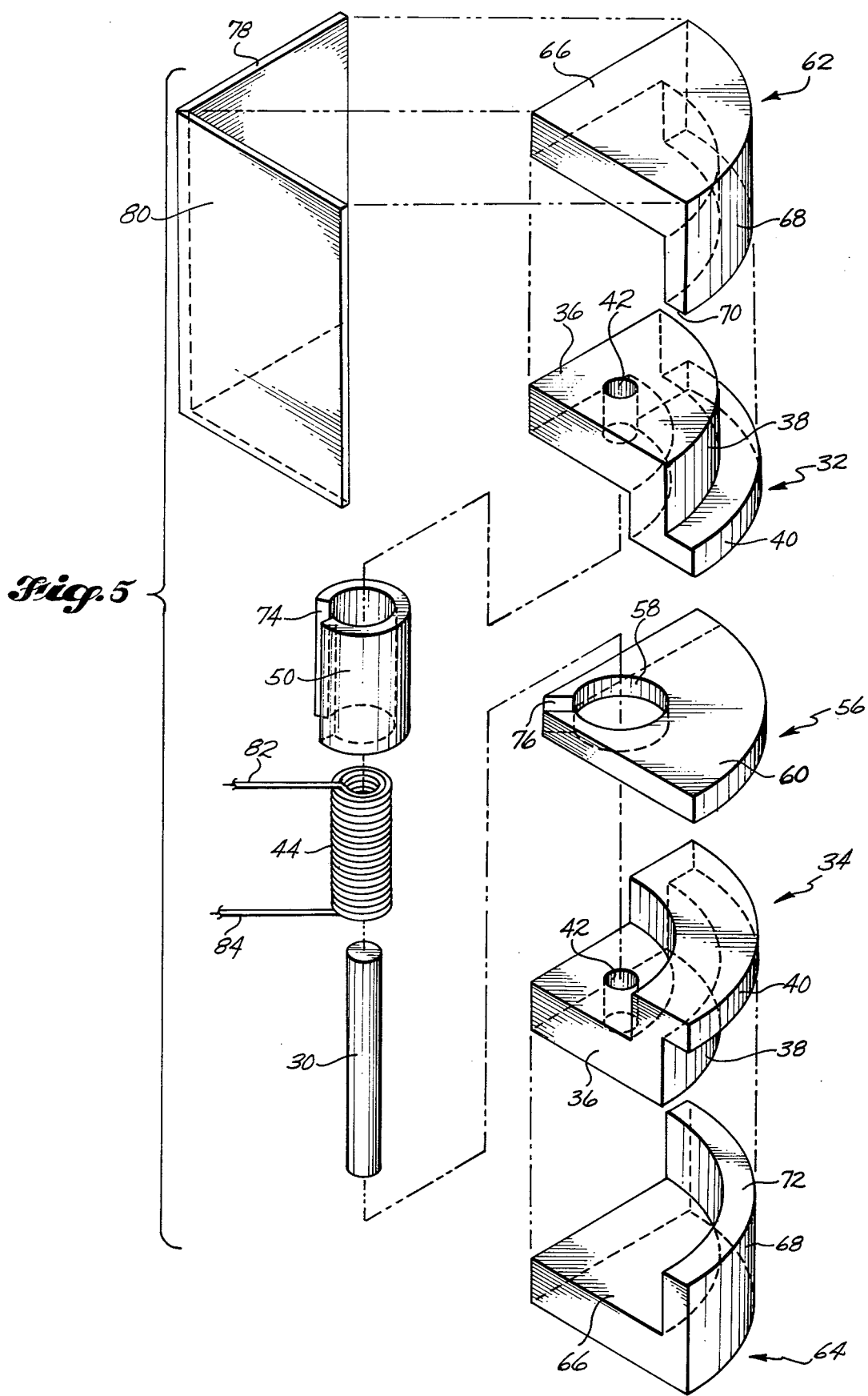

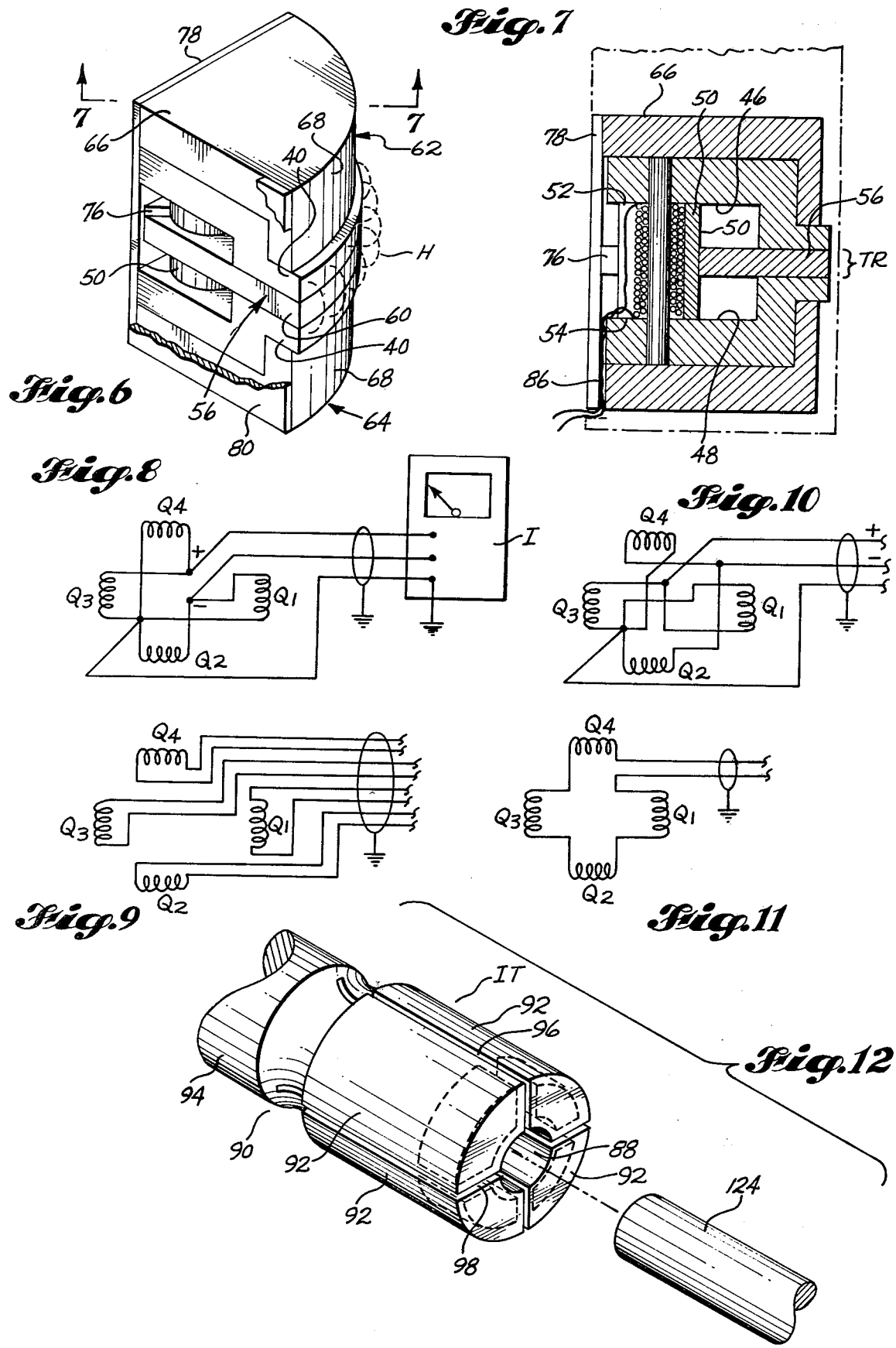

EDDY-CURRENT TEST PROBE WITH SEGMENTED CIRCUMFERENTIAL TEST GAP AND METHOD FOR INSPECTION OF MATERIALS

BACKGROUND OF THE INVENTION

1. Field of the Invention

The present invention relates to controlled reluctance, eddy-current generator type material inspection apparatus and methods, and more particularly to eddy-current probes or tools which are especially adapted for inspecting metal tubing, fastener holes, rods and similar geometries.

2. Cross-Reference to Related Application

The present invention is related to the invention described in copending application Ser. No. 741,666, filed Nov. 15, 1976, and entitled EDDY-CURRENT FLUX GENERATOR FOR TESTING OR MATERIAL, in the both inventions involve the use of high and low reluctance materials to concentrate the reluctance of exciting coils in the material to be tested and to control the spatial extent of the generated eddy currents.

3. Discussion of the Prior Art

The aforementioned application Ser. No. 741,666 commences with a quite detailed discussion of eddy-current testing techniques and a comparison of the invention to which such application relates with specific prior art devices. Application Ser. No. 741,666 also includes a quite detailed explanation of the use of high and low reluctance materials together to (1) concentrate the reluctance of the eddy-current generator in the material to be tested and (2) control the spatial extent and shape of generated eddy currents. For background purposes, reference should be made to the complete disclosure of U.S. application Ser. No. 741,666, the contents of which are hereby incorporated herein by this specific reference.

U.S. application Ser. No. 741,666, the several patents mentioned therein, and the prior art that was cited and considered by the Patent Office, both with respect to such application and its predecessor (Ser. No. 538,955, now abandoned), should be consulted for the purpose of properly evaluating the subject invention and putting it into proper perspective.

Particular patents which should be considered are U.S. Pat. No. 3,430,134, granted Feb. 25, 1969 to John J. Flaherty and Richard M. Soble, and entitled Weld Tracker System Having Magnetically Isolated Pickup Coils and U.S. Pat. No. 3,840,802, granted Oct. 8, 1974 to Phillip L. Anthony. These patents involve the use of a plurality of eddy-current generators in a single probe or sensing apparatus.

Glossary of Terms

Electromagnetic skin depth: A characteristic parameter of a material which at any given frequency of operation depends only on the conductivity and permeability of that material. It is a measure of the penetration depth of the electromagnetic field.

High reluctance material: A material which at the operating frequency of the exciting coil during material testing use has an electromagnetic skin depth which is substantially less than the effective flux path length through the material.

Low reluctance material: A material which at the operating frequency of the exciting coil during material testing use has an electromagnetic skin depth which is substantially greater than the effective flux path length through the material.

Parallel reluctance: The effective reluctance which controls the flux which does not pass through the material being evaluated.

SUMMARY OF THE INVENTION

Eddy-current generators of the invention described herein are essentially characterized by:
1. A segmented design and construction, with each segment comprising an eddy-current generator providing a circumferential segment of a test gap region.
2. An eddy-current generator construction characterized by:
   (a) a low reluctance core and low reluctance field guides;
   (b) an exciting coil of high conductivity wire which is wound on the low reluctance core;
   (c) high reluctance materials combined with such low reluctance materials in such a manner as to essentially eliminate the parallel contribution to the reluctance of the eddy-current generator and concentrate the reluctance of the coil in the material to be tested.

An external sheathing of high reluctance material, adapted to eliminate the interaction of stray electromagnetic fields between the several eddy-current generators is sometimes important.

According to an important aspect of the invention, the several eddy-current generators are mounted in such a manner that they are independently radially movable in position by contact with the material to be tested. As a result, they are able to maintain a nearly one hundred percent fill factor even when passing the test probe through or over structures having varying diameters or shapes. For example, a test probe for inspecting the inside of tubing and/or fastener holes having different diameters may be constructed in four parts or quadrants and include an eddy-current generator in each quadrant. Each eddy-current generator is supported by means allowing it to move radially in response to differences in dimension of the material being tested. For example, an inspection probe incorporating this aspect of the invention and constructed to inspect the inside of tubing and/or fastener holes can be used for inspecting fastener holes having different diameters, or for inspecting tubing having dents, constrictions, ovalization, and other variations in the tubing diameter.

These and other objects, advantages and features of eddy-current generator test probes constructed in accordance with the present invention will be apparent from the description of the illustrated embodiments.

BRIEF DESCRIPTION OF THE DRAWING

In the drawing like letters and numerals refer to like parts, and:

FIG. 1 is an isometric view of a first embodiment of the invention shown in spaced alignment with a fastener hole;

FIG. 2 is a view looking towards the head of the probe of FIG. 1, showing the probe inside of a first size fastener hole;

FIG. 3 is a view like FIG. 2, but showing the probe inside of a smaller size fastener hole;

FIG. 4 is an exploded side elevational view of the probe shown by FIG. 1;

FIG. 5 is an exploded isometric view of one of the eddy-current generators;

FIG. 6 is an assembled isometric view of one of the eddy-current generators, with a foreground portion of one of the side plates removed;

FIG. 7 is an axial sectional view of the eddy-current generator shown by FIG. 6, taken substantially along line 7—7 of FIG. 6;

FIG. 8 is a schematic diagram of a four part probe, with two adjacent eddy-current generators wired in parallel;

FIG. 9 is a view similar to FIG. 8, but showing each eddy-current generator wired separately;

FIG. 10 is a view like FIGS. 8 and 9, but showing opposite eddy-current generators wired in parallel;

FIG. 11 is a view like FIGS. 8, 9 and 10, but showing all four eddy-current generators connected in series;

FIG. 12 is an isometric view of a second embodiment, comprising radially inwardly directed gap regions, and a central passageway for receiving the outside diameter of a length of tubing or the like;

DESCRIPTION OF THE PREFERRED EMBODIMENT

Figure 14:
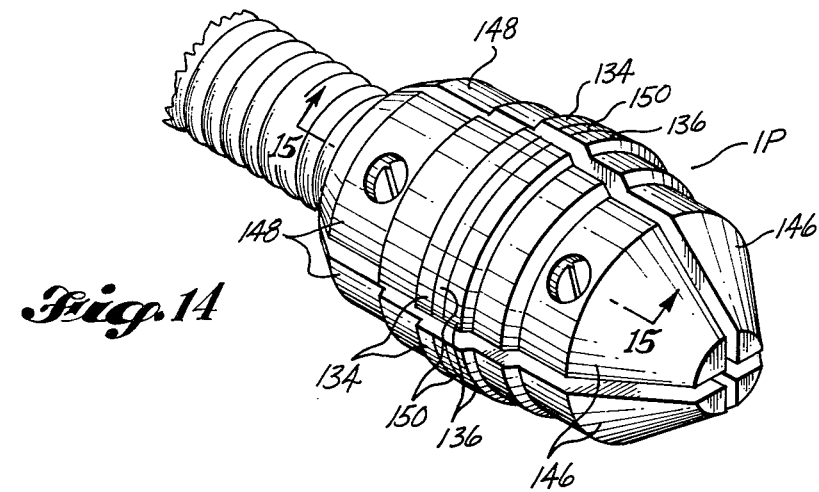
FIG. 14 is an isometric view of another embodiment of the invention.

Referring to FIGS. 1 and 2, the first embodiment of the invention, which is an internal probe P, comprises a body 10 made from a plastic or other material. A cavity 12 is formed in the forward end of body 10 and body 10 is slotted throughout a substantial portion of its length at 14 and 16. Slots 14, 16 extend axially of body 10 and are perpendicular to each other, so as to divide body 10 into four axially elongated parts between the slots. Slots 14, 16 also divide cavity 12 into four parts. An axial passageway 18 extends from a floor region of each recess part rearwardly through body 10, to serve as a lead wire avenue.

Four identical eddy-current generators 20 are housed within the four sections of the cavity 12. As will hereinafter be described in more detail, lead wires extend rearwardly through these passageways 18 from the eddy-current generators 20 to the rear end 24 of body 10, whereat they are suitably connected to wires within a cable 22 which connects the probe to an eddy-current test instrument or impedance bridge I (FIG. 8).

Preferably, the probe P includes a hemispherical head 26 which is also divided by slots 14', 16', so that it also comprises four sections 28.

During manufacture, the four eddy-current generators 20 are glued into place, each within a section of the sectional cavity 12. Then, a head section 28 is glued onto the forward side of each eddy-current generator. When the probe is assembled, slots 14', 16' are extensions of the slots 14, 16 and the head parts 28 are extensions of the body parts defined by and between the slots 14, 16.

As shown by FIGS. 1 and 4, a thin wall or skin of the body material surrounds and protects the gap regions of the eddy-current generators. The head 26 serves to both protect the eddy-current generators and to help guide the probe P into a fastener hole FH or the like. The slots 14, 14', 16, 16' permit some contraction of the eddy-current generator carrying parts of body 10, so that the probe P can be inserted into a slightly undersized hole FH' (FIG. 3).

Referring now to FIGS. 5-7, each eddy-current generator 20 comprises a core 30 and a pair of magnetic field guides 32, 34, all constructed from a low reluctance material. As best shown by FIGS. 5 and 7, the core 30 is an elongated solid cylindrical member. Magnetic field guides 32, 34 are identical and have a sectorial general form. Each comprises a sectorial end wall 36, a peripheral wall 38 which is a segment of an annulus. Each end wall 36 includes an axial opening 42 sized to snugly receive an end portion of the core 30. As best shown by FIG. 7, in an assembled eddy-current generator 20 the two magnetic field guides 32, 34 and the core 30 are integral.

Insulated wire is wrapped around core 30, in between the two inner faces 46, 48 of the magnetic field guides 32, 34, to form an exciting coil 44. The number of coil turns is selected to match the impedance requirements of the test instrument. A sleeve 50 of high reluctance material concentrically surrounds coil 44. The sleeve 50 of high reluctance material extends throughout the full length of the coil 44 and its end surfaces 52, 54 abut against the inner surfaces 46, 48 of the magnetic field guides 32, 34.

A sectorial plate 56, constructed from a high reluctance material, extends radially outwardly from the high reluctance sleeve 50. As best shown by FIG. 5, plate 56 includes an opening 58 in which the sleeve 50 is snugly received. Plate 56 includes a gap portion 60 which conforms in shape to the flange portions 40 of the two magnetic field guides 32, 34. As best shown by FIG. 7, in an assembled eddy-current generator 20 the gap portion 60 of plate 56 is sandwiched between the flange portions 40 of the two magnetic field guides 32, 34. The peripheral surfaces of the two flanges 40 and the peripheral surface of gap plate 56 are substantially flush.

A pair of identical end caps 62, 64 are provided axially outwardly of the two magnetic field guides 32, 34. End caps 62, 64 are also constructed from a high reluctance material and they conform in shape to the magnetic field guides 32, 34. Each cap 62, 64 comprises a sectorial end wall 66 and a peripheral wall 68 which is a segment of a cylinder. As best shown by FIGS. 6 and 7, in an assembled eddy-current generator 20 the end walls 66 are situated axially outwardly of the end walls 56 and the cylindrical walls 68 are situated radially outwardly of the cylindrical walls 38. An axial space or gap is defined between the end surfaces 70, 72 of the two walls 68. The two flanges 40 and the peripheral portion of plate 56 sandwiched therebetween substantially fills such space and projects radially outwardly beyond the peripheral surfaces of walls 68.

Sleeve 50 is formed to include a longitudinal slot 74 and gap plate 56 is formed to include a slot 76.

Each side of the eddy-current generator 20 is covered by a wall 78, 80 of high reluctance material. Thus, the side walls 78, 80 and the end caps 62, 64 provide an external sheathing of high reluctance material which is broken only in the region of the projecting flange portions 40 of the magnetic field guides 32, 34. Lead wires 82, 84 extend from the opposite ends of the coil 44 through the gap 74 and then to and through an avenue 86 formed through a corner apex region of the sheathing, as shown by FIG. 7, and then outwardly from the eddy-current generator 20.

The illustrated embodiment comprises a low reluctance core 30 and low reluctance magnetic field guides 32, 34 made from manganese zinc ferrite. However, it is to be understood that any low reluctance material can be used. A used herein, the term "low reluctance material" means a material having a skin depth which is much larger than the magnetic path length.

The low reluctance core 30 provides a low reluctance path for the magnetic field from the coil 44 to the magnetic field guides 32, 34. The magnetic field guides 32, 34 provide a low reluctance path for the magnetic field from the core 30 to the material M to be tested.

The gap plate 56 is made of a high reluctance material and is used to essentially prevent the magnetic field from passing directly between the two field guides 32, 34 without passing through the test region TR (FIGS. 4 and 7). The thickness of member 56 controls the size of the test region TR. The plate member 56 in the illustrated embodiment is copper; however, any high reluctance material may be used.

As used herein, the expression "high reluctance material" means any electrical conducting material which at the frequency of operation has an electromagnetic skin depth which is much smaller than the magnetic path length through the material.

The end caps 66 and the side wall 78, 80 are also made from a high reluctance material and are used to reduce the coupling between adjacent segments. High reluctance sleeve 50 helps guide the magnetic flux from the coil to the magnetic field guides 32, 34.

The four eddy-current generators 20 of the illustrated embodiment together define a four-part discontinuous gap extending circumferentially about the probe P. The time varying current in the coils 44 generates a time varying magnetic field H in the shape of a toroid extending from one low reluctance flange 40 to the other, and bridging across the peripheral portion 60 of the high reluctance material 56 in the gap between such flanges 40 (FIG. 6).

The depth of penetration of the circumferential eddy-currents generated in the wall of the material to be tested are controlled by the frequency of operation as well as the thickness of the material 56.

Inspection by use of the probe P is accomplished by moving the probe through the fastener hole FH (or through the inside of tubing) and the impedance of the coil is monitored as the eddy-current generator 20 is moved through the test piece. Variations in the impedance are a measure of material variation (e.g., flaws, cracks, pits, and other defects within the test piece).

The segmented probe shown by FIGS. 1–7 and described above is only one way of advantageously employing the invention. Such embodiment is constructed for internal testing of holes or tubing in which only minor variations in inside diameter are encountered. As will hereinafter be described in greater detail, the segments can be spring mounted for a greater amount of radial movement when the probe is to be used for internal inspection of materials involving greater variances in the inside diameter. Thus, one advantage of the segmented probe is that the diameter of the probe is not fixed as in a single unit construction but may be varied.

A second advantage of the multi-segment construction of the probe is that the segments may be electrically connected in several ways:

(1) Each segment can be electrically independent with the probe operated in the absolute mold for testing purposes. A circuit of this type is shown by FIG. 9. The four coils for the four eddy-current generators 20 are separately designated Q1, Q2, Q3, Q4. The lead wires for such coils all extend into the cable which leads back to the eddy-current test instrument I.

(2) Each segment can be connected in series with the probe operated in the absolute mold for testing purposes. A circuit of this type is shown by FIG. 11.

(3) Pairs of segments can be connected together and matched against a second identical pair; the two sets are, for example, connected to opposite sides of an impedance bridge. For example, in a four segment bracket (quadrant construction) two adjacent generators can be connected in parallel to form pairs of dual-segment generators (FIG. 8); these dual-segment pairs are then connected to each side of the impedance bridge and the probe is operated in a differential mode for testing purposes. Similarly, diametrically opposite generators can be connected in parallel to form pairs of two-segment generators (FIG. 10); these two-segment pairs are connected to opposite sides of an impedance bridge and the probe is operated in the differential mode for testing purposes.

(4) Each segment can be operated in the differential mode for testing purposes.

By operating in a differential mode such as described in (3) and (4) above, signals from structural variations with planar symmetry in the case of wiring described in (3) and fourfold symmetry in the case of wiring as described in (4), are generally reduced. Hence, when one is interested in testing for defects in the vicinity of such structural variations, these wiring configurations can have a great advantage over non-segmented designs.

FIG. 12 shows an inspection tool IT which is basically like the tool shown by FIGS. 1–7 except that the test gap is directed radially inwardly, into a central axial passageway 88 which extends at least part way through the tool IT. The tool IT includes a body 90 having a plurality of beam portions 92 extending in parallelism from a common base 94. As in the first embodiment, the beam portions 92 are separated by slots 96, 98. In this embodiment, as in the first embodiment, each body portion 92 occupies a quadrant and each houses an eddy-current generator 100.

Figure 13:
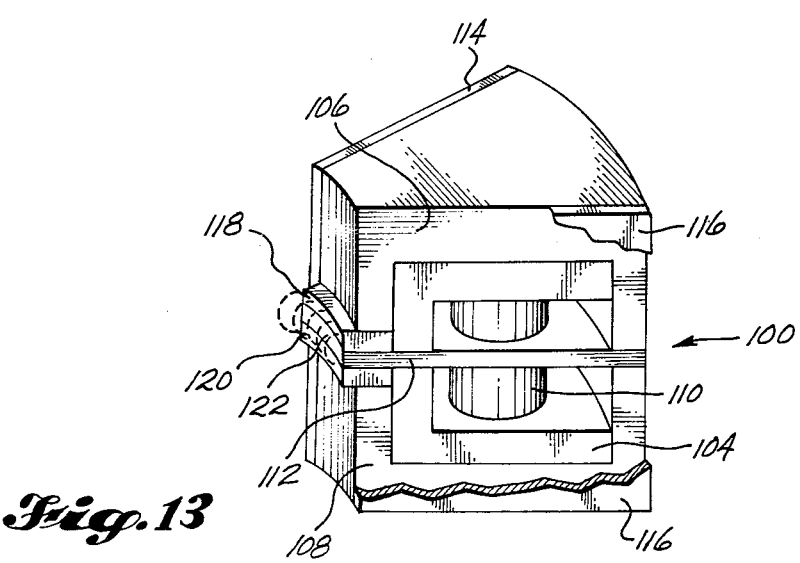
FIG. 13 is a view like FIG. 6, but of an eddy-current generator from the inspection fixture shown by FIG. 12.

As shown by FIG. 13, each eddy-current generator is constructed much like an eddy-current generator 20, except that the test gap region forming components are directed radially inwardly. Each generator 100 includes a core (not shown) and a pair of magnetic field guides 102, 104, all constructed from a low reluctance material. End caps 106, 108 constructed from a high reluctance material are positioned axially outwardly of the magnetic flux guides 102, 104. A sleeve of high reluctance material 110 surrounds the coil and a plate member 112 constructed from high reluctance material extends radially of the sleeve 110. Side plates 114, 116, both constructed from a high reluctance material, complete a high reluctance casing for the high reluctance generator 100 which is interrupted only by the radially inwardly protruding portions 118, 120 of the low reluctance magnetic field guides 102, 104. The radial inner surfaces of these portions 118, 120 are substantially flush with the radial inner surface 122 of the high reluctance gap member 112. Such surfaces form a cylindrical segment. As in the earlier embodiment, the test gap is a circumferential segment. Collectively, the test gaps of the several eddy-current generators 100 define a discontinuous circumferential gap.

As in the embodiment shown by FIGS. 1-7, the mounting of the eddy-current generators 100 within beam portions 92 of the tool body 90 permit a limited amount of radial movement of the eddy-current generators 100. The diameter of passageway 88 is selected to be no larger than the smallest diameter of a member 124 which is to be inspected. Then, when the member 124 is inserted into passageway 88, if it has a slightly larger diameter or is not perfectly round, for example, it will force one or more of the support beams 92 radially outwardly as it is moved relatively through the passageway 88.

Any one of the manners of connecting the eddy-current generators 100 to the read-out instrument I, that is shown by FIGS. 8-11, can be used with the inspection tool IT shown by FIGS. 12 and 13. The selection will depend on the objectives of the inspection procedure.

Figure 15:
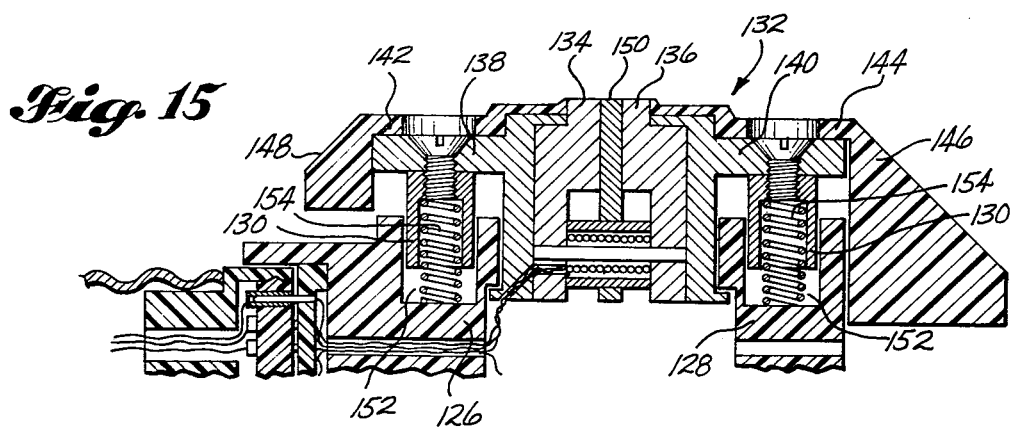
FIG. 15 is an enlarged scale axial section view taken substantially along line 15—15 of FIG. 14.

FIGS. 14 and 15 disclose another embodiment of the invention which is designed to accommodate greater variances in diameter. This particular embodiment is also in the form of an internal probe IP.

As best shown by FIG. 15, the probe IP includes two axially spaced apart inner body portions 126, 128 which are constructed from a dielectric material. This embodiment is also shown to be divided into four parts or quadrants (FIG. 14). Each internal body part 126, 128 is formed to include four radial sockets 130 spaced ninety degrees apart. The probe IP includes four eddy-current generators 132 which are constructed like the eddy-current generators in the above described two embodiments. Therefore, a detailed description of all parts of the generators will not be repeated.

In this embodiment the low reluctance magnetic field guides 134, 136 are axially outwardly bounded by high reluctance end caps 138, 140 which include cylindrical segments 142, 144 which are disposed radially outwardly from the inner body parts 126, 128. A plastic nose piece 146 encloses the forward end cap 140 and projects forwardly from the body member 128, to constitute a nose piece for the probe IP. A plastic cover 148 surrounds the rear end cap 138 and completes a plastic cover for the probe IP. Peripheral portions of the magnetic field guides 134, 136 and a peripheral portion 150 of a high reluctance gap plate member project outwardly into an axial space defined between the two shell members 146, 148. As in the earlier embodiments, collectively the exposed portions of the magnetic field guides 134, 136 and the gap plate member 150 for the several eddy-current generators define a discontinuous test gap region which extends circumferentially around the probe IP.

In this embodiment, a tubular sleeve 152 is housed within each socket 130 and a compression spring 154 is located within each sleeve 152. Countersunk flathead screws 156 extend through openings in the dielectric shell parts and the high reluctance end caps, and thread into the threaded outer ends of the sleeves 152. This construction results in the two shell parts 146, 148 being integrally attached to the eddy-current generator 132 and mounts such assembly for limited radial movement relative to the internal body parts 126, 128. A pair of stop members 158 retain the eddy-current generator segments on the internal body parts 126, 128.

As in the other embodiments, a cable containing lead wires from the several exciting coils extends rearwardly from the probe IP to a suitable read-out instrument I.

Although each of the embodiments involves a four segment design, the invention is not limited to a four segment design; the probe could be made up in any number of segments.

What is claimed is:

1. An eddy-current inspection tool, comprising:
   a plurality of eddy-current generators angularly grouped about an axis;
   each said eddy-current generator comprising:
   an inner body of low reluctance material, including:
   an elongated core part which is parallel to and spaced radially outwardly from said axis,
   a first magnetic field guide extending generally radially at one end of said core part, and
   a second magnetic field guide extending generally radially at the second end of said core part, said magnetic field guides being apart axially at a common radial boundary of said eddy-current generator, to form an axial gap;
   an exciting coil of insulated electrically conductive wire surrounding said core part;
   high reluctance material surrounding said coil and extending radially from said coil into said axial gap and terminating substantially even with gap bordering surface portions of said first and second magnetic field guides, said surface portions and said axial gap together forming a circumferential test region which in use is positioned contiguous the material being tested; and
   external sheathing of high reluctance material on said eddy-current generator except at the circumferential test region,
   said high reluctance materials being positioned to substantially eliminate the parallel reluctance of said coil.

2. An eddy-current inspection tool according to claim 1, wherein external sheathing is positioned on the eddy-current generators to substantially eliminate the interaction of stray electromagnetic fields between the several eddy-current generators.

3. An eddy-current inspection tool according to any one of claims 1 or 2, wherein the circumferential test region forming parts of the magnetic field guides and the high reluctance material therebetween are directed radially outwardly.

4. An eddy-current inspection tool according to claims 1 or 2, wherein the circumferential test region forming parts of the magnetic field guides and the high reluctance material therebetween are directed radially inwardly.

5. An eddy-current inspection tool according to any one of claims 1 or 2, in which the tool comprises support means for the eddy-current generators serving to mount the eddy-current generators for a limited amount of independent movement in the radial direction.

6. An eddy-current inspection tool according to claim 5, wherein the circumferential test region forming parts of the magnetic field guides and the high reluctance material therebetween are directed radially outwardly.

7. An eddy-current inspection tool according to claim 5, wherein the circumferential test region forming parts of the magnetic field guides and the high reluctance material therebetween are directed radially inwardly.

8. An eddy-current inspection probe according to claim 5, wherein said tool includes a body having a base portion and a plurality of beam portions extending in parallel with each other from the base portion, said beam portions being separated by gaps, so that each beam portion can deflect radially inwardly, and each said beam portion carrying a said eddy-current generator.

9. An eddy-current inspection probe according to claim 5, wherein said probe comprises front and rear inner body portions and plurality of axially elongated outer body portions, each including a said eddy-current generator, bridging across the inner body portions and being separated from each other by gaps, and spring mounting means between the inner and outer body parts, mounting the outer body portions and the eddy-current generators carried thereby, for limited radial movement relative to the inner body parts.

10. Eddy-current type inspection apparatus for material testing use, comprising:
an inspection probe comprising:
- a plurality of eddy-current generators angularly grouped about an axis;
- each said eddy-current generator comprising:
    an inner body of low reluctance material, including:
    an elongated core part which is parallel to and spaced radially outwardly from said axis,
    a first magnetic field guide extending generally radially at one end of said core part, and
    a second magnetic field guide extending generally radially at the second end of said core part,
    said magnetic field guides being spaced apart axially at a common radial boundary of said eddy-current generator, to form an axial gap;
    an exciting coil of insulated electrically conductive wire surrounding said core part;
    high reluctance material surrounding said coil and extending radially from said coil into said axial gap and terminating substantially even with gap bordering surface portions of said first and second magnetic field guides, said surface portions and said axial gap together forming a circumferential test region which in use is positioned contiguous the material being tested; and
    external sheathing of high reluctance material on said eddy-current generator except at the circumferential test region,
    said high reluctance materials being positioned to substantially eliminate the parallel reluctance of said coil; and alternating current means connected to said coils, for operating each said coil at a suitable frequency for the particular material testing to be done.

11. An eddy-current type inspection apparatus for material testing use according to claim 10, wherein external sheathing is positioned on the eddy-current generators to substantially eliminate the interaction of stray electromagnetic fields between the several eddy-current generators.

12. Eddy-current inspection apparatus according to any of claims 10 or 11, wherein the circumferential test region forming parts of the magnetic field guides and the high reluctance material therebetween are directed radially outwardly.

13. Eddy-current inspection apparatus according to any one of claims 10 or 11, wherein the circumferential test region forming parts of the magnetic field guides and the high reluctance material therebetween are directed radially inwardly.

14. Eddy-current inspection apparatus according to any one of claims 10, 11 or 12, in which the tool comprises support means for the eddy-current generators serving to mount the eddy-current generators for a limited amount of independent movement in the radial direction.

15. Eddy-current inspection apparatus according to claim 14, wherein the circumferential test region forming parts of the magnetic field guides and the high reluctance material therebetween are directed radially outwardly.

16. Eddy-current inspection apparatus according to claim 14, wherein the circumferential test region forming parts of the magnetic field guides and the high reluctance material therebetween are directed radially inwardly.

17. Eddy-current inspection apparatus according to claim 14, wherein said tool includes a body having a base portion and a plurality of beam portions extending in parallel with each other from the base portion, said beam portions being separated by gaps, so that each beam portion can deflect radially inwardly, and each said beam portion carrying a said eddy-current generator.

18. Eddy-current inspection apparatus according to claim 14, wherein said probe comprises front and rear inner body portions and a plurality of axially elongated outer body portions, each including a said eddy-current generator, bridging across the inner body portions and being separated from each other by gaps, and spring mounting means between the inner and outer body parts, mounting the outer body portions and the eddy-current generators carried thereby, for limited radial movement relative to the inner body parts.

19. A method of inspecting a generally cylindrical shaped material, comprising:
- locating a plurality of eddy-current generators adjacent to the surface of said material, each of which presents a circumferentially extending test segment including an axial gap, so that together the circumferential test segments form a discontinuous, circumferential test gap region;
- separately biasing each test gap segment into contact with the adjacent portion of the material being inspected;
- operating each eddy-current generator to produce magnetic flux across the test gap and in the material to be inspected;
- combining high reluctance and low reluctance materials in the eddy-current generators for the purpose of concentrating the reluctance of each eddy-current generator in the material being inspected; and
- monitoring the eddy-current generators to determine characteristics of the material being inspected.

20. A method according to claim 19, comprising operating each eddy-current generator independently of the others in the absolute mode.

21. A method according to claim 19, comprising connecting all of the eddy-current generators in series and operating them in the absolute mode.

22. A method according to claim 19, comprising employing four eddy-current generators and connecting adjacent generators in parallel to form pairs of dual-segment generators.

23. A method according to claim 22, comprising connecting the dual-segment pairs to opposite sides of an impedance bridge and operating them in a differential mode.

24. A method according to claim 21, comprising utilizing four eddy-current generators and connecting opposite generators in parallel to form pairs of two-segment generators.

25. A method according to claim 24, comprising connecting the two-segment pairs of opposite sides of an impedance bridge and operating them in the differential mode.

26. A method according to claim 19, comprising operating each eddy-current generator in the differential mode.

* * * * *